(12) United States Patent
Kawamura

(10) Patent No.: US 11,234,641 B2
(45) Date of Patent: Feb. 1, 2022

(54) BODY FAT PERCENTAGE MEASUREMENT DEVICE, METHOD AND PROGRAM

(71) Applicant: FUJIFILM Corporation, Tokyo (JP)

(72) Inventor: Takahiro Kawamura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 399 days.

(21) Appl. No.: 15/904,436

(22) Filed: Feb. 26, 2018

(65) Prior Publication Data

US 2018/0263559 A1    Sep. 20, 2018

(30) Foreign Application Priority Data

Mar. 16, 2017  (JP) .............................. JP2017-051473
Jul. 10, 2017   (JP) .............................. JP2017-135065

(51) Int. Cl.
  A61B 6/00     (2006.01)
  A61B 5/00     (2006.01)
  G06T 7/00     (2017.01)
  A61B 6/03     (2006.01)
  A61B 5/0537   (2021.01)

(52) U.S. Cl.
  CPC ............ *A61B 5/4872* (2013.01); *A61B 6/032* (2013.01); *A61B 6/4266* (2013.01); *A61B 6/482* (2013.01); *A61B 6/5217* (2013.01); *G06T 7/0012* (2013.01); A61B 5/0537 (2013.01); A61B 5/7264 (2013.01); G06T 2207/10081 (2013.01)

(58) Field of Classification Search
  CPC ... A61B 5/0537; A61B 5/4872; A61B 5/7264; A61B 6/032; A61B 6/4266; A61B 6/482; A61B 6/5217; G06T 2207/10081; G06T 7/0012
  See application file for complete search history.

(56) References Cited

U.S. PATENT DOCUMENTS

| 8,385,622 B2 | 2/2013 | Goto et al. |
| 2003/0090389 A1* | 5/2003 | Maeda ................. A61B 5/0537 324/692 |
| 2011/0158386 A1* | 6/2011 | Payne ...................... G06T 7/11 378/54 |

(Continued)

FOREIGN PATENT DOCUMENTS

| JP | 2004147863 | 5/2004 |
| JP | 2015192846 | 11/2015 |
| WO | 2009017004 | 2/2009 |

OTHER PUBLICATIONS

"Office Action of Japan Counterpart Application," with machine English translation thereof, dated Jan. 14, 2020, p. 1-p. 6.

*Primary Examiner* — Mark D Remaly
(74) *Attorney, Agent, or Firm* — JCIPRNET

(57) ABSTRACT

A subtraction processing unit generates a soft portion image representing a soft portion tissue of a subject from first and second radiation images. A body thickness estimation unit estimates a body thickness distribution of the subject on the basis of imaging conditions in a case where the soft portion image and the first and second radiation images are acquired. An approximate body thickness distribution calculation unit calculates an approximate body thickness distribution obtained by approximating the estimated body thickness distribution to a model corresponding to a human body, and a body fat percentage calculation unit calculates a distribution of a body fat percentage in the subject on the basis of the approximate body thickness distribution.

6 Claims, 7 Drawing Sheets

(56) References Cited

U.S. PATENT DOCUMENTS

2015/0257740 A1\* 9/2015 Horinaka ............. A61B 8/5223
600/437
2016/0081654 A1\* 3/2016 Sarnow ................... G06T 7/155
600/438
2016/0354051 A1 12/2016 Enomoto et al.

\* cited by examiner

BODY FAT PERCENTAGE MEASUREMENT DEVICE, METHOD AND PROGRAM

CROSS-REFERENCE TO RELATED APPLICATIONS

The present application claims priority under 35 U.S.C. § 119 to Japanese Patent Applications of No. 2017-051473, filed on Mar. 16, 2017 and No. 2017-135065, filed on Jul. 10, 2017. Each of the above application(s) is hereby expressly incorporated by reference, in its entirety, into the present application.

BACKGROUND OF THE INVENTION

1. Field of the Invention

The present invention relates to a body fat percentage measurement device, method, and a non-transitory computer readable recording medium storing a program for measuring a body fat percentage of a subject.

2. Description of the Related Art

In the related art, an electrical impedance method is known as a scheme for measuring a body fat percentage. The electrical impedance method is a scheme for measuring a proportion of body fat in a total body weight of a subject as a single value. Therefore, in the electrical impedance method, how the body fat is distributed in the subject cannot be recognized. Therefore, a scheme of capturing a tomographic image of a subject in order to acquire a distribution of the body fat in the subject and measuring the distribution of the body fat in the tomographic image has been proposed (see WO2009/017004A).

SUMMARY OF THE INVENTION

However, in the scheme described in WO2009/017004A, the tomographic image is required in order to measure the distribution of the body fat. In order to acquire the tomographic image, it is necessary to irradiate the subject multiple times with radiation. Accordingly, the amount of exposure to radiation of the subject increases. Further, since it is necessary to acquire the tomographic image, work for body fat measurement becomes complicated.

The present invention has been made in view of the above circumstances, and an object of the present invention is to easily measure a body fat percentage of a subject while reducing the amount of exposure to radiation of the subject.

A body fat percentage measurement device according to the present invention comprises a subtraction processing unit that generates a soft portion image representing a soft portion tissue of a subject from a plurality of radiation images acquired using radiations having different energy distributions transmitted through the subject; a body thickness estimation unit that estimates a body thickness distribution of the subject on the basis of imaging conditions in a case where the soft portion image and the radiation image are acquired; approximate body thickness distribution calculation unit that calculates an approximate body thickness distribution obtained by approximating the estimated body thickness distribution to a model corresponding to a human body; and a body fat percentage calculation unit that calculates a distribution of a body fat percentage in the subject on the basis of the approximate body thickness distribution.

In the body fat percentage measurement device according to the present invention, the body fat percentage calculation unit may further calculate the distribution of the body fat percentage on the basis of the estimated body thickness distribution.

Further, in the body fat percentage measurement device according to the present invention, the body thickness estimation unit may generate a low frequency image of the soft portion image, and estimate the body thickness distribution of the subject on the basis of the low frequency image of the soft portion image and the imaging conditions.

Further, the body fat percentage measurement device according to the present invention may further comprise a display control unit that displays the distribution of the body fat percentage on a display unit.

Further, in the body fat percentage measurement device according to the present invention, the display control unit may display the distribution of the body fat percentage to be superimposed on any one of the plurality of radiation images and the soft portion image.

A body fat percentage measurement method according to the present invention comprises: generating a soft portion image representing a soft portion tissue of a subject from a plurality of radiation images acquired using radiations having different energy distributions transmitted through the subject; estimating a body thickness distribution of the subject on the basis of imaging conditions in a case where the soft portion image and the radiation image are acquired; calculating an approximate body thickness distribution obtained by approximating the estimated body thickness distribution to a model corresponding to a human body; and calculating a distribution of a body fat percentage in the subject on the basis of the approximate body thickness distribution.

The body fat percentage measurement method according to the present invention may be provided as a non-transitory computer readable recording medium storing a program for causing a computer to execute the body fat percentage measurement method.

Another body fat percentage measurement device according to the present invention includes a memory that stores instructions that a computer is caused to execute, and a processor configured to execute the stored instructions, and the processor executes a subtraction process of generating a soft portion image representing a soft portion tissue of a subject from a plurality of radiation images acquired using radiations having different energy distributions transmitted through the subject; a body thickness estimation process of estimating a body thickness distribution of the subject on the basis of imaging conditions in a case where the soft portion image and the radiation image are acquired; an approximate body thickness distribution calculation process of calculating an approximate body thickness distribution obtained by approximating the estimated body thickness distribution to a model corresponding to a human body; and a body fat percentage calculation process of calculating a distribution of a body fat percentage in the subject on the basis of the approximate body thickness distribution.

According to the present invention, the soft portion image representing a soft portion tissue of a subject is generated from a plurality of radiation images acquired using radiations having different energy distributions transmitted through the subject, and the body thickness distribution of the subject is estimated on the basis of the imaging conditions in a case where the soft portion image and the radiation image are acquired. The approximate body thickness distribution obtained by approximating the estimated body thickness distribution to a model corresponding to a human body is calculated, and the distribution of a body fat percentage in the subject is calculated on the basis of the approximate body thickness distribution. Therefore, it is possible to measure the distribution of the body fat percentage of the subject with a small number of times of imaging, and thereby, it is possible to reduce the amount of exposure to radiation of the subject and easily measure the body fat percentage of the subject.

DESCRIPTION OF THE PREFERRED EMBODIMENTS

Figure 1:
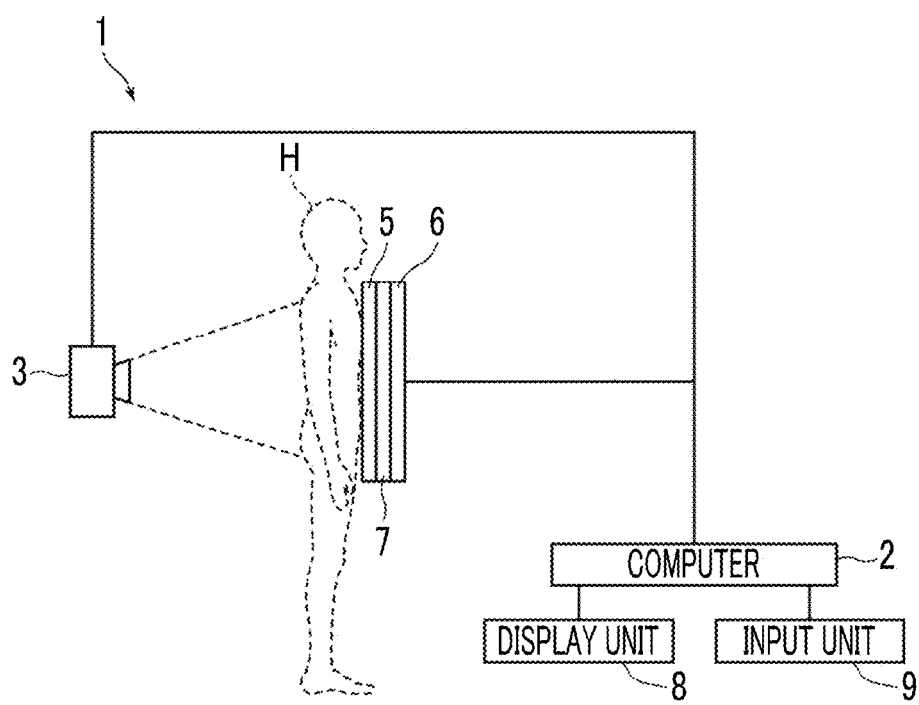
FIG. 1 is a schematic block diagram illustrating a configuration of a radiation image capturing system to which a body fat percentage measurement device according to an embodiment of the present invention is applied.

Hereinafter, embodiments of the present invention will be described with reference to the drawings. FIG. 1 is a schematic block diagram illustrating a configuration of a radiation image capturing system to which a body fat percentage measurement device according to an embodiment of the present invention is applied. As illustrated in FIG. 1, the radiation image capturing system according to the embodiment captures two radiation images having different energy distributions, performs an energy subtraction process using the two radiation images, and measures a body fat percentage using a soft portion image acquired through the process. The radiation image capturing system includes an imaging device 1, and a computer 2 including the body fat percentage measurement device according to the embodiment.

The imaging device 1 is an imaging device for performing so-called one-shot energy subtraction for irradiating a first radiation detector 5 and a second radiation detector 6 with X-rays emitted from an X-ray source 3 that is a radiation source and transmitted through a subject H with different energies. At the time of imaging, the first radiation detector 5, an X-ray energy conversion filter 7 made of a copper plate or the like, and the second radiation detector 6 are arranged in order from the side close to the X-ray source 3 as illustrated in FIG. 1, and the X-ray source 3 is driven. The first and second radiation detectors 5 and 6 and the X-ray energy conversion filter 7 are in close contact with each other.

Thus, in the first radiation detector 5, a first radiation image G1 of the subject H according to low-energy X-rays including so-called soft rays is acquired. In the second radiation detector 6, a second radiation image G2 of the subject H according to high-energy X-rays from which the soft rays have been removed is acquired. The first and second radiation images are input to the computer 2 which is a body fat measurement device.

The first and second radiation detectors 5 and 6 are capable of repeatedly recording and reading a radiation image. A so-called direct type radiation detector that generates charges by directly receiving the irradiation may be used, or a so-called indirect type radiation detector which first converts the radiation into visible light and converts the visible light into a charge signal may be used. Further, as a scheme of reading a radiation image signal, it is desirable to use a so-called TFT reading scheme in which a radiation image signal is read by turning a thin film transistor (TFT) switch on and off, or a so-called optical reading scheme in which a radiation image signal is read by performing irradiation with reading light, but the present invention is not limited thereto, and other schemes may be used.

A display unit 8 and an input unit 9 are connected to the computer 2. The display unit 8 includes a cathode ray tube (CRT), a liquid crystal display, or the like, and performs assistance of various inputs necessary for radiation images acquired by imaging and a process that is performed on the computer 2. The input unit 9 includes a keyboard, a mouse, a touch panel, or the like. The display unit 8 corresponds to a display unit.

A body fat percentage measurement program of the embodiment is installed on the computer 2. In the embodiment, the computer may be a work station or a personal computer that the operator directly operates, or may be a server computer connected to the work station or the personal computer over a network. The body fat percentage measurement program is recorded and distributed on a recording medium such as a digital versatile disc (DVD) or a compact disc read only memory (CD-ROM), and is installed on the computer from the recording medium.

Alternatively, the body fat percentage measurement program is stored in a storage device of a server computer connected to a network or in a network storage in a state in which the body fat percentage measurement program is accessible from the outside, downloaded to the computer in response to a request, and installed.

Figure 2:
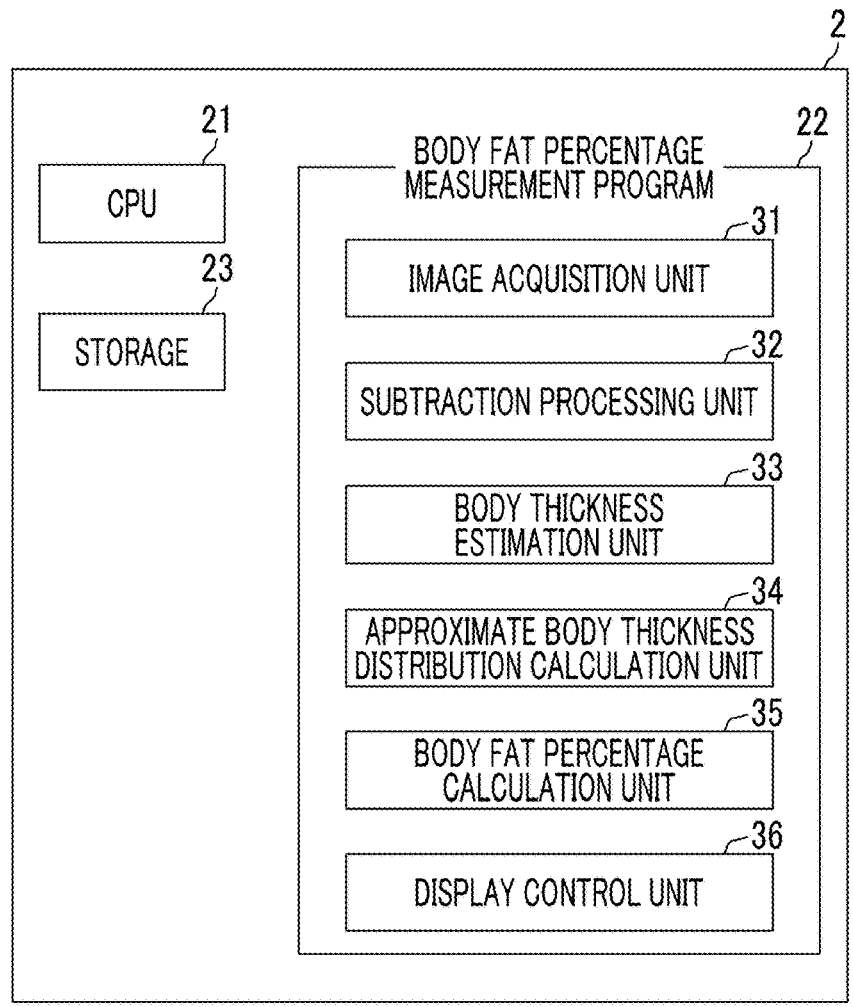
FIG. 2 is a diagram illustrating a schematic configuration of the body fat percentage measurement device according to the embodiment.

FIG. 2 is a schematic configuration of a body fat percentage measurement device realized by installing the body fat percentage measurement program on the computer 2 in the embodiment. As illustrated in FIG. 2, the body fat percentage measurement device includes a central processing unit (CPU) 21, a memory 22, and a storage 23 as a standard computer configuration.

The storage 23 is a storage device such as a hard disk or a solid state drive (SSD), and stores various types of information including a program for driving each unit of the imaging device 1 and the body fat percentage measurement program. Further, the radiation image acquired by imaging is stored.

The memory 22 temporarily stores a program or the like stored in the storage 23 to cause the CPU 21 to execute various processes. The body fat percentage measurement program defines, as processes that the CPU 21 is caused to execute, an image acquisition process of causing the imaging device 1 to perform imaging and acquiring first and second radiation images G1 and G2 having different energy distributions, a subtraction process of generating a soft portion image Gs representing a soft portion tissue of the subject H from the first and second radiation images G1 and G2, a body thickness estimation process of estimating the body thickness distribution of the subject H on the basis of imaging conditions in a case where the soft portion image Gs, the first radiation image G1, and the second radiation image G2 are acquired, an approximate body thickness distribution calculation process of calculating an approximate body thickness distribution obtained by approximating the estimated body thickness distribution to a model corresponding to a human body, a body fat percentage calculation process of calculating a distribution of the body fat percentage in the subject H based on the approximate body thickness distribution, and a display control process for displaying the distribution of the body fat percentage on the display unit 8.

By the CPU 21 executing these processes according to the body fat percentage measurement program, the computer 2 functions as an image acquisition unit 31, a subtraction processing unit 32, a body thickness estimation unit 33, an approximate body thickness distribution calculation unit 34, a body fat percentage calculation unit 35, and a display control unit 36. The computer 2 may include a processor or a processing circuit that performs each of the image acquisition process, the subtraction process, the body thickness estimation process, the approximate body thickness distribution calculation process, the body fat percentage calculation process, and the display control process.

The image acquisition unit 31 drives the X-ray source 3 to irradiate the subject H with X-rays, detects the X-rays transmitted through the subject H using the first and second radiation detectors 5 and 6, and acquires the first and second radiation images G1 and G2. In this case, imaging conditions such as the amount of imaging rays, a tube voltage, and an SID are set. The imaging conditions may be set by an input from the input unit 9 by the operator. The set imaging conditions are stored in the storage 23. The first and second radiation images G1 and G2 may be acquired using a program separate from the body fat percentage measurement program and stored in the storage 23. In this case, the image acquisition unit 31 reads the first and second radiation images G1 and G2 stored in the storage 23 from the storage 23 for image processing. In the embodiment, it is assumed that the first and second radiation images G1 and G2 for a portion from a chest to an abdomen of the subject H are acquired by imaging the portion from the chest to the abdomen.

Figure 3:
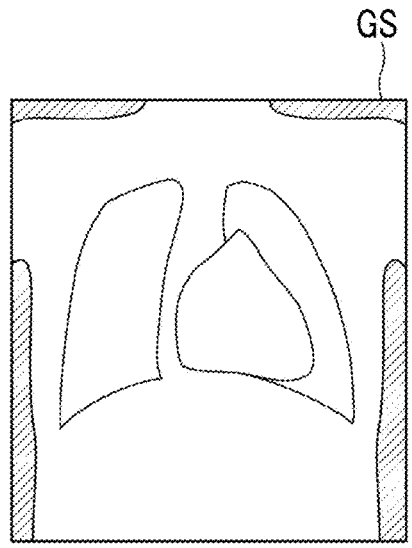
FIG. 3 is a diagram illustrating a soft portion image.

The subtraction processing unit 32 generates a subtraction image obtained by extracting a specific structure of the subject H included in each of the radiation images G1 and G2 by performing weighted subtraction between corresponding pixels on the first radiation image G1 and the second radiation image G2. In the embodiment, the first and second radiation images G1 and G2 are radiation images of the portion from the chest to the abdomen. The subtraction processing unit 32 appropriately performs weighting on the first radiation image G1 and the second radiation image G2 and performs the subtraction to generate a soft portion image Gs obtained by extracting only the soft portion of the subject H. FIG. 3 is a diagram illustrating the soft portion image Gs.

The body thickness estimation unit 33 estimates the body thickness distribution of the subject H on the basis of the imaging conditions in a case where the soft portion image Gs and the first and second radiation images G1 and G2 are acquired. In a case where the body thickness distribution is estimated, the body thickness estimation unit 33 generates a low-frequency soft portion image GLs representing a low frequency component of the soft portion image Gs. Specifically, the body thickness estimation unit 33 performs a filtering process using a low pass filter on the soft portion image Gs to generate the low-frequency soft portion image GLs. The low-frequency soft portion image GLs may be generated using a well-known scheme such as wavelet transformation and Fourier transformation.

Figure 4:
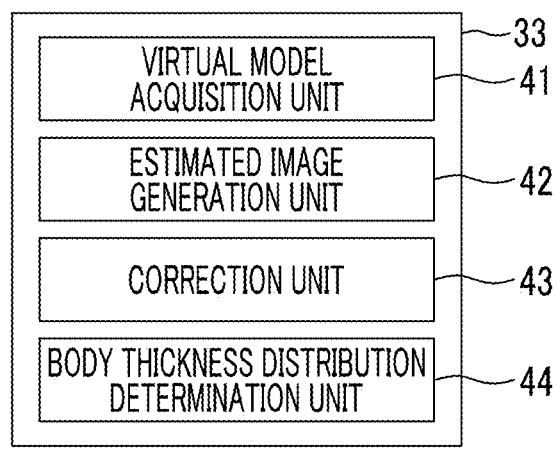
FIG. 4 is a schematic block diagram illustrating a configuration of a body thickness estimation unit.

In the embodiment, the body thickness estimation unit 33 estimates the body thickness distribution of the subject H using a scheme described in, for example, JP2015-043959A. FIG. 4 is a schematic block diagram illustrating a configuration of the body thickness estimation unit 33. As illustrated in FIG. 4, the body thickness estimation unit 33 includes a virtual model acquisition unit 41, an estimated image generation unit 42, a correction unit 43, and a body thickness distribution determination unit 44.

The virtual model acquisition unit 41 acquires a virtual model K of the subject H having an initial body thickness distribution T0(x, y).

The estimated image generation unit 42 generates an image obtained by combining an estimated primary ray image Igp obtained by estimating a primary ray image obtained by imaging the virtual model K with an estimated scattered ray image Igs obtained by estimating a scattered radiation image obtained by imaging the virtual model K, on the basis of the virtual model K, as an estimated image Im obtained by estimating the low-frequency soft portion image GLs obtained by imaging the subject H and obtained through a subtraction process.

The correction unit 43 corrects the initial body thickness distribution T0 of the virtual model K so that a difference between the estimated image Im and the low-frequency soft portion image GLs is reduced, on the basis of the estimated image Im and the low-frequency soft portion image GLs.

The body thickness distribution determination unit 44 determines the corrected body thickness distribution Tn−1 (n is a natural number) as a body thickness distribution T(x, y) of the low-frequency soft portion image GLs.

In the embodiment, the virtual model K of the subject H having the initial body thickness distribution T0(x, y) is stored in the storage 23. Further, the process that is performed by the body thickness estimation unit 33 will be described in detail below.

The approximate body thickness distribution calculation unit 34 calculates an approximate body thickness distribution Tcylin(x, y) obtained by approximating the body thickness distribution estimated by the body thickness estimation unit 33 to a model corresponding to the human body. In the embodiment, an elliptic cylinder model having an elliptical cross-section is assumed to be used as the model corresponding to the human body. Specifically, the approximate body thickness distribution calculation unit 34 generates an initial elliptic cylinder model in which initial values of a long diameter and a short diameter of the cross-section of the elliptic cylinder model are set, and corrects the initial values of the long diameter and the short diameter of the cross-section of the initial elliptic cylinder model so that an error from a body thickness distribution (x, y) determined by the body thickness distribution determination unit 44 is minimized. The approximate body thickness distribution calculation unit 34 generates an elliptic cylinder model having an elliptical cross-section with the corrected long diameter and short diameter. A body thickness distribution in the generated elliptic cylinder model is the approximate body thickness distribution Tcylin(x, y).

The body fat percentage calculation unit 35 calculates the distribution of the body fat percentage of the subject H on the basis of the approximate body thickness distribution Tcylin(x, y). Here, in a body trunk portion of the human body, a cross-section in a body axis direction of the human body can approximate to a substantially elliptical shape. The approximated elliptical shape is the approximate body thickness distribution Tcylin(x, y). In this case, a product of an attenuation coefficient μsoft of the soft portion tissue of the human body and the approximate body thickness distribution Tcylin(x, y) indicates a change in density due to X-ray attenuation due to the soft portion tissue on the low-frequency soft portion image GLs. The change in density indicates a change from a density that is obtained by the X-rays reaching the radiation detectors 5 and 6 without being transmitted through the subject H. Therefore, a distribution of the change in density on the image is calculated by subtracting a density of each pixel in an area of the subject H from a density in a void area obtained by directly irradiating the radiation detectors 5 and 6 with the X-rays in the low-frequency soft portion image GLs. Hereinafter, the distribution of the change in density on the image is referred to as a density difference distribution Δ(x, y).

Figure 5:
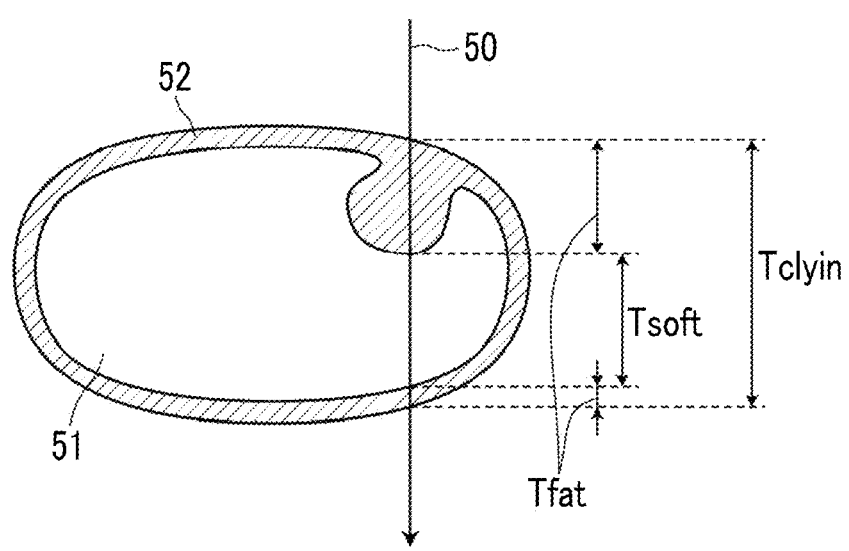
FIG. 5 is a cross-sectional view taken along a plane perpendicular to a body axis of a subject.

On the other hand, as illustrated in FIG. 5, a fat 52 is included on an X-ray transmission path of an actual subject indicated by an arrow 50, in addition to the soft portion tissue 51. Therefore, the density difference distribution Δ(x, y) is expressed as Equation (1) below using an attenuation coefficient μfat of the fat, a thickness distribution Tfat(x, y) of the fat, an attenuation coefficient μsoft of the soft portion tissue other than the fat, and a thickness distribution Tsoft(x, y) of the soft portion tissue.

[Equation 1]

$$\Delta(x,y) = \mu_{fat} \times T_{fat}(x,y) + \mu_{soft} \times T_{soft}(x,y) \quad (1)$$

Further, a relationship of Tcylin(x, y)=Tfat(x, y)+Tsoft(x, y) is satisfied. Therefore, the body fat percentage R(x, y) at each pixel position (x, y) in the low-frequency soft portion image GLs can be calculated using Equation (2) below.

[Equation 2]

$$r(x, y) = \frac{T_{fat}(x, y)}{T_{cylin}(x, y)} \quad (2)$$

$$= \frac{\mu_{soft} - \frac{\Delta(x, y)}{T_{cylin}(x, y)}}{\mu_{soft} - \mu_{fat}}$$

Figure 6:
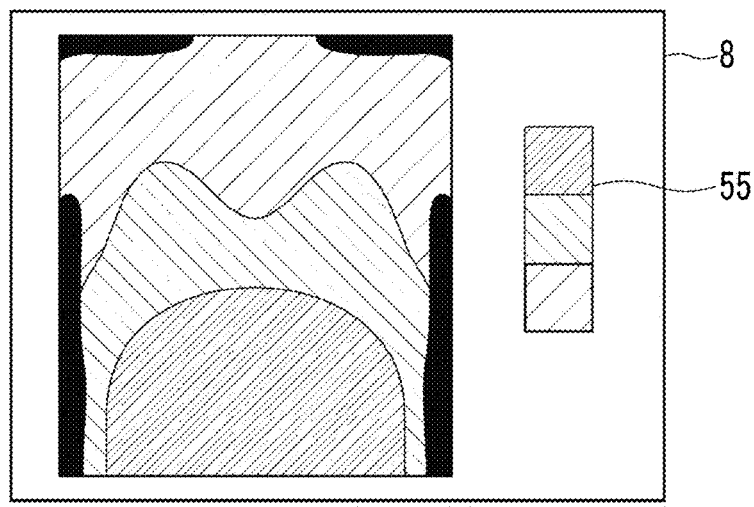
FIG. 6 is a diagram illustrating a body fat percentage distribution displayed on a display unit.

The display control unit 36 displays the body fat percentage distribution calculated by the body fat percentage calculation unit 35 on the display unit 8. FIG. 6 is a diagram illustrating the body fat distribution displayed on the display unit 8. As illustrated in FIG. 6, in the embodiment, the body fat percentage distribution is displayed to be superimposed on the first radiation image G1. The body fat percentage distribution may be superimposed on the second radiation image G2 or the soft portion image Gs. In FIG. 6, the body fat percentage distribution is color-classified into three colors and displayed. In FIG. 6, the color classification is represented by a difference in density, and it is shown that the larger the density, the higher the body fat percentage becomes. Further, a reference 55 representing a relationship between the density and the body fat percentage is displayed on the display unit 8. By referring to the reference 55, the distribution of the body fat percentage can be easily recognized.

Figure 7:
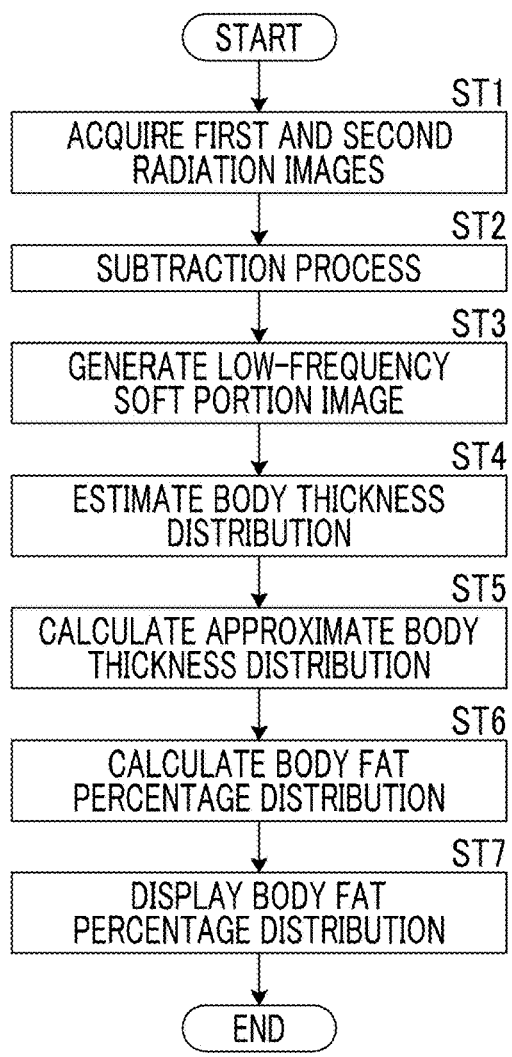
FIG. 7 is a flowchart illustrating a process that is performed in the embodiment.

Next, a process that is performed in the embodiment will be described. FIG. 7 is a flowchart illustrating a process that is performed in the embodiment. First, the image acquisition unit 31 causes the imaging device 1 to capture images and acquires the first and second radiation images G1 and G2 having different energy distributions (step ST1). Then, the subtraction processing unit 32 performs the subtraction process to generate the soft portion image Gs representing the soft portion tissue of the subject H from the first and second radiation images G1 and G2 (step ST2). The body thickness estimation unit 33 generates the low-frequency soft portion image GLs from the soft portion image Gs (step ST3), and estimates the body thickness distribution T(x, y) of the subject H on the basis of the imaging conditions in a case where the low-frequency soft portion image GLs and the first and second radiation images G1 and G2 are acquired (step ST4). The approximate body thickness distribution calculation unit 34 calculates an approximate body thickness distribution obtained by approximating the estimated body thickness distribution T(x, y) to an elliptic cylinder model (step ST5), and the body fat percentage calculation unit 35 calculates a distribution of the body fat percentage in the subject H on the basis of the approximate body thickness distribution (step ST6). The display control unit 36 displays the distribution of the body fat percentage on the display unit 8 (step ST7), and the process ends.

Figure 8:
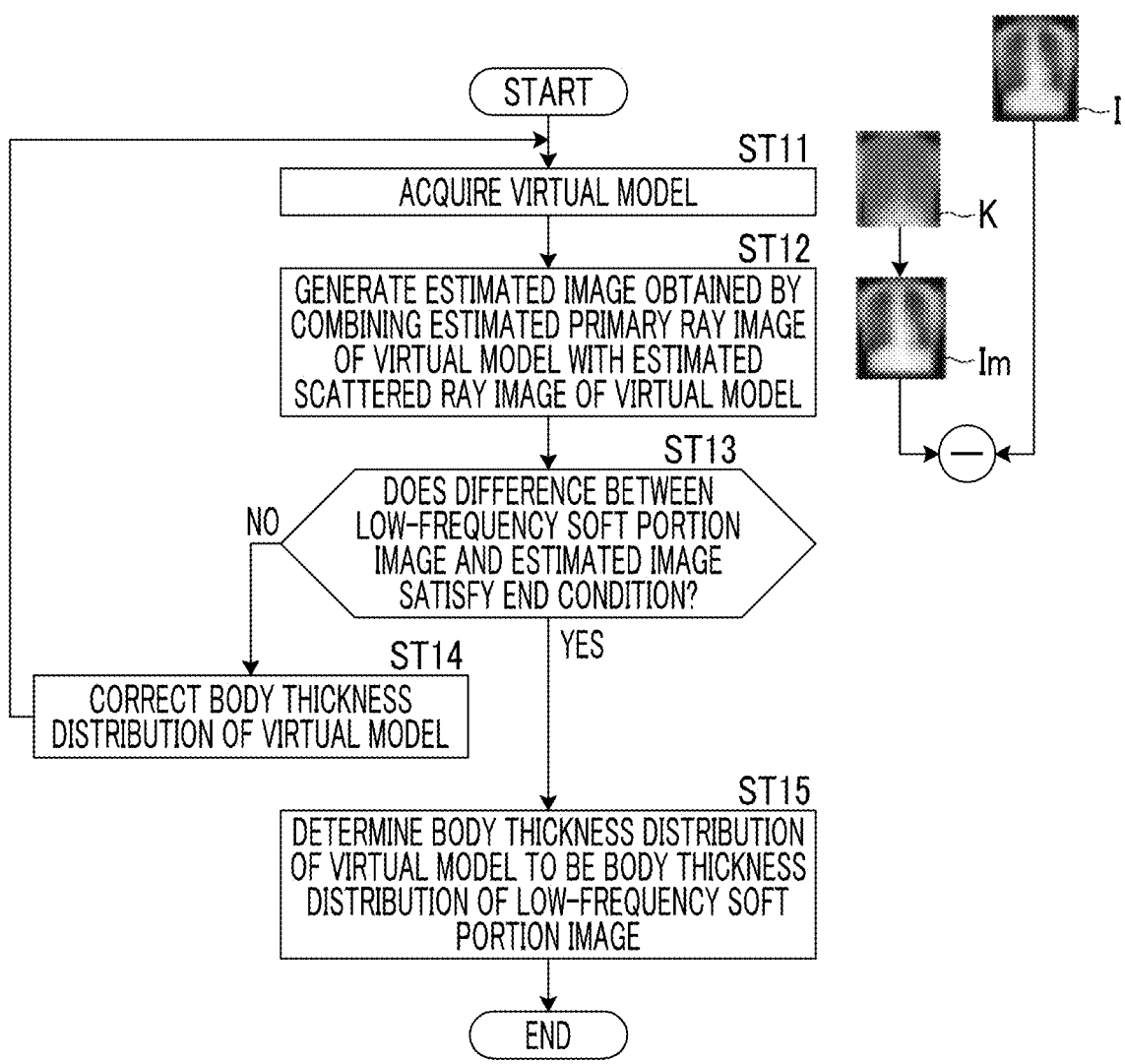
FIG. 8 is a flowchart of a body thickness estimation process.

Next, the body thickness estimation process will be described. FIG. 8 is a flowchart of the body thickness estimation process. The virtual model acquisition unit 41 of the body thickness estimation unit 33 acquires the virtual model K of the subject H having the initial body thickness distribution T0(x, y) from the storage 23 (step ST11). The virtual model K is data virtually representing the subject H in which the body thickness according to the initial body thickness distribution T0(x, y) is associated with each position on an xy plane. Further, a structure included in the virtual model K (an anatomical structure such as a bone or an organ), an arrangement of the structure, characteristic information indicating characteristics of the structure with respect to radiation, and the like are set on the basis of an arrangement and a composition of the anatomical structure such as a bone or an organ of a comparative subject.

Figure 9:
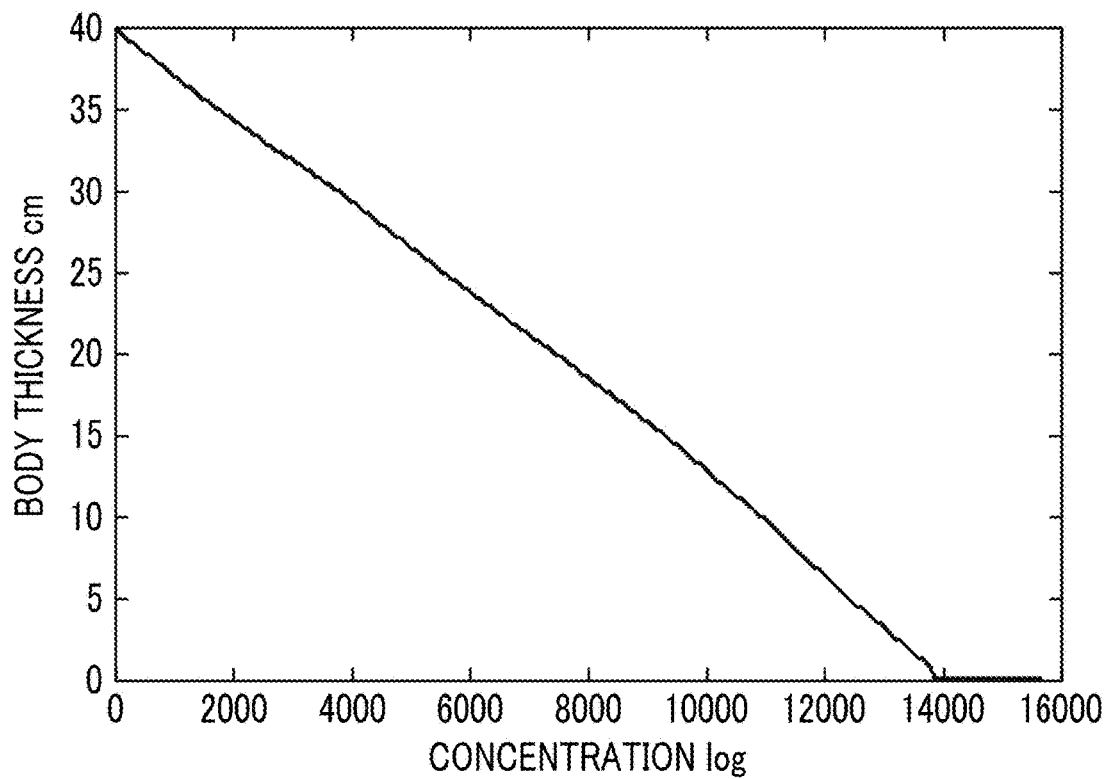
FIG. 9 is a diagram illustrating an example of an association table of a body thickness distribution.

Further, the initial body thickness distribution T0(x, y) of the virtual model K may be an arbitrary distribution, but in the embodiment, the initial body thickness distribution T0 is generated and acquired by the virtual model acquisition unit 41. The virtual model acquisition unit 41 acquires imaging conditions such as the amount of imaging rays, a tube voltage, and an SID of the subject H, and acquires a table in which a pixel value according to the imaging conditions of the subject H is associated with the body thickness from the storage 23. FIG. 9 illustrates an example of a table in which the pixel value is associated with the body thickness. The virtual model acquisition unit 41 acquires the body thickness distribution of the radiation image by specifying the body thickness corresponding to the pixel value of each pixel of the radiation image of the subject H on the basis of the table illustrated in FIG. 9. The virtual model acquisition unit 41 acquires the body thickness distribution of the radiation image as the initial body thickness distribution T0 of the virtual model K. The initial body thickness distribution T0 may be generated at the time of a process of acquiring the virtual model K as in this embodiment or may be set in advance prior to the process of acquiring the virtual model K. The above process is expressed by Equation (3) below. I(x, y) indicates the pixel value of each pixel in the radiation image, and T0(x, y) indicates the initial body thickness distribution at each pixel position.

[Equation 3]

$$T_0(x,y) = LUT(I(x,y)) \quad (3)$$

Figure 10:
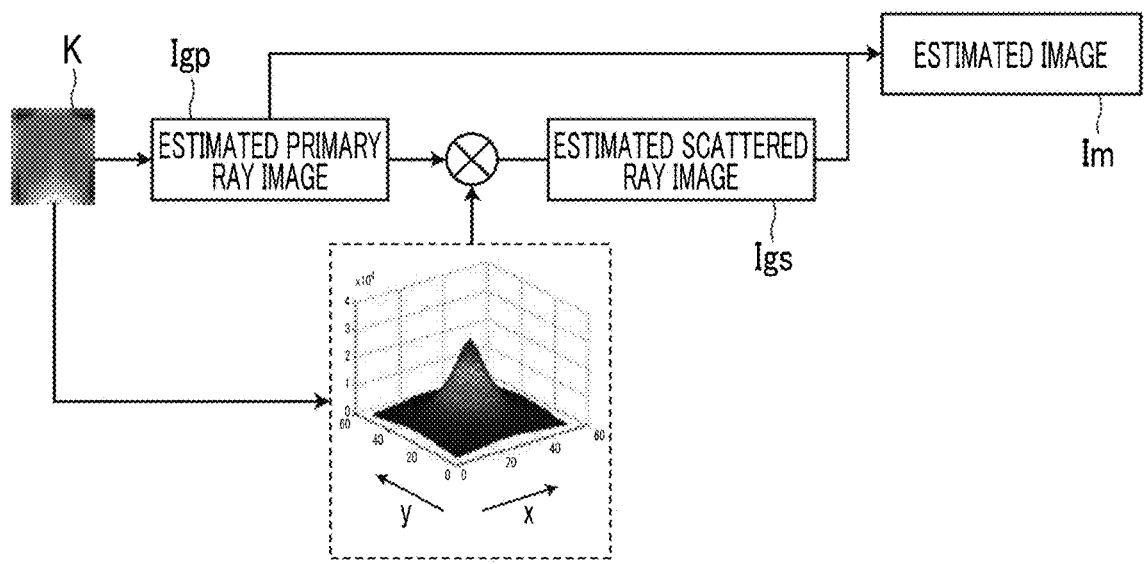
FIG. 10 is a diagram illustrating an example of a method of generating an estimated image.
Figure 11:
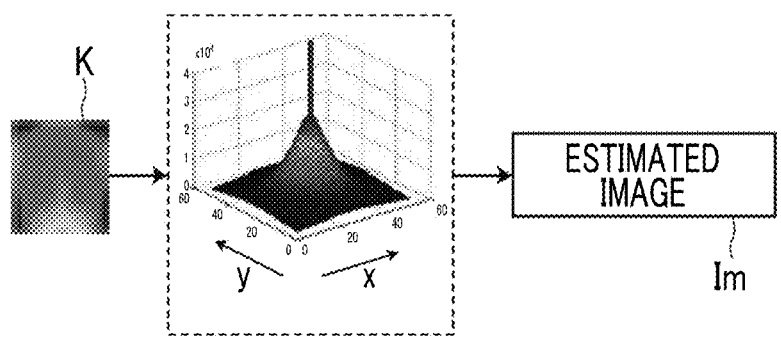
FIG. 11 is a diagram illustrating another example of a method for generating an estimated image.

Then, the estimated image generation unit 42 generates the estimated image Im obtained by combining the estimated primary ray image Igp obtained in a case where the virtual model K is imaged under the same imaging conditions as those for the radiation image with the estimated scattered ray image Igs obtained in a case where the virtual model K is imaged under the same imaging condition as those of the radiation image (step ST12). FIGS. 10 and 11 are diagrams illustrating a method of generating the estimated image Im.

As illustrated in FIG. 10, the estimated image generation unit 42 generates the estimated primary ray image Igp that is obtained in a case where the virtual model K is imaged under the same imaging conditions as those for the low-frequency soft portion image GLs, that is, the first and second radiation images G1 and G2 according to Equation (4) below, and generates the estimated scattered ray image Igs according to Equation (5) using the generated estimated primary ray image Igp. The estimated image generation unit 42 generates the estimated image Im by combining the estimated primary ray image Igp with the estimated scattered ray image Igs as shown in Equation (6) (step ST12). In a case where the estimated primary ray image Igp and the estimated scattered ray image Igs are generated for the first time, the initial body thickness distribution T0(x, y) is used in the estimation equations (4) and (5) (n=1 in Equation (4) and (5)).

[Equation 4]

$$I_{gp}(x, y) = I_o(x, y) \times \exp(-T_{n-1}(x, y) \times \mu) \quad (4)$$

$$I_{gs}(x, y) = \sum_{x',y'} I_{gp}(x', y') K_s(x, y, T_{n-1}(x', y'), \theta_{x',y'}) \quad (5)$$

$$I_m(x, y) = I_{gp}(x, y) + I_{gs}(x, y) \quad (6)$$

Here, (x, y) is coordinates of the pixel position of the low-frequency soft portion image GLs, Igp(x, y) is an estimated primary ray image at the pixel position (x, y), Igs(x, y) is the estimated scattered ray image at the pixel position (x, y), Io(x, y) is the amount of rays at the pixel position (x, y), Im(x, y) is the estimated image at the pixel position (x, y), μ is a ray attenuation coefficient of the subject H, and Ks(x, y, Tn(x', y'), θx', y') is a convolution kernel representing a point spread function according to a subject thickness at the pixel position (x, y). The amount of rays Io(x, y) is the amount of rays of radiation that is detected by the radiation detector 5 in a case where it is assumed that there is no subject H, and is changed according to a distance (SID) between the X-ray source 3 and a detection surface of the radiation detector 5, the tube voltage, and an mAs value. Further, θx',y' represents a parameter that is specified using imaging conditions such as a tube voltage or characteristic information of the virtual model K.

The estimated image Im may be an image that is estimated to be obtained in a case where the virtual model K is radiographed, or may be substantially regarded as an image obtained by combining the estimated primary ray image Igp with the estimated scattered ray image Igs. For example, as illustrated in FIG. 11, the estimated image Im may be generated by performing convolution integral on a kernel obtained by combining a primary ray component with a scattered radiation component using Equation (7) below instead of Equations (4) to (6). Here, Kp+s(x, y, Tn−1(x', y'), θx', y') is a kernel representing a point spread function obtained by combining the primary ray component with the scattered ray component. Further, any model function may be used as long as an estimated image obtained by combining the estimated primary ray image with the estimated scattered ray image can be generated from the image obtained by imaging.

Ks(x, y, Tn(x', y'), θx',y') and Kp+s(x, y, Tn−1 (x', y'), θx',y') can be obtained experimentally according to the imaging conditions or the like.

Although the kernels Ks(x, y, Tn(x', Y'), θx',y') and Kp+s (x, y, Tn−1(x', y'), θx',y') may be calculated on the basis of imaging conditions at the time of imaging in the embodiment, a table in which various imaging conditions are associated with the kernels Ks(x, y, Tn(x', Y'), θx',y') and Kp+s (x, y, Tn−1(x', y'), θx',y') may be stored in the storage 23, and the kernels Ks(x, y, Tn(x', Y'), θx',y') and Kp+s (x, y, Tn−1(x', y'), θx',y') may be obtained by referring to this table on the basis of irradiation field information at the time of imaging, the subject information, and the imaging conditions.

[Equation 5]

$$I_m(x, y) = \sum_{x',y'} K_{p+s}(x, y, T_{n-1}(x', y'), \theta_{x',y'}) \quad (7)$$

A subsequent process will be described with reference to the flowchart of FIG. 8. Subsequently, the body thickness distribution determination unit 44 determines whether or not a difference between the low-frequency soft portion image GLs and the estimated image Im satisfies an end condition (step ST13). Here, as shown in Equations (8) and (9), an error value Verror representing the difference between the low-frequency soft portion image GLs and the estimated image Im below is defined, and it is determined whether or not the error value Verror is equal to or smaller than a threshold value, as the end condition. Further, as shown in Equation (9), a sum of squares of respective pixel values of a differential image Id obtained by subtracting the estimated image Im from the low-frequency soft portion image GLs is defined as an error function ferror. Any determination scheme capable of determining that the difference between the low-frequency soft portion image GLs and the estimated image Im has been sufficiently small to an allowable extent can be applied as the end condition.

[Equation 6]

$$V_{error} = f_{error}(I_m(x, y), I(x, y)) \quad (8)$$

$$f_{error}(I_m(x, y), I(x, y)) = \sum_{x,y} (I_m(x, y) - I(x, y))^2 \quad (9)$$

Further, the present invention is not limited to the above example, and the error function ferror can be defined using any method for indicating the difference between the low-frequency soft portion image GLs and the estimated image Im. For example, as shown in Equation (10), a sum of absolute values of the respective pixel values of the differential image Id obtained by subtracting the estimated image Im from the low-frequency soft portion image GLs may be used as the error function ferror.

[Equation 7]

$$f_{error}(I_m(x, y), I(x, y)) = \sum_{x,y} |I_m(x, y) - I(x, y)| \quad (10)$$

In a case where the error value Verror does not satisfy the end condition (step ST13: No), the body thickness distribution determination unit 44 performs a correction process of correcting the body thickness distribution Tn−1 (the initial body thickness distribution T0 in the case of n=1) (step ST14).

An arbitrary method capable of acquiring a correction value of each position of the body thickness distribution Tn−1 so that the difference between the low-frequency soft portion image GLs and the estimated image Im is reduced in order to perform the process of correcting the body thickness distribution Tn−1 can be applied. In this embodiment, a process of changing the body thickness distribution Tn−1 of the virtual model K for each partial area of one or more pixels of the virtual model K and calculating the body thickness of the partial area to reduce a difference between the estimated image Im and the low-frequency soft portion image GLs is performed. The body thickness distribution of the virtual model is corrected with the calculated body thickness of each partial area.

Specifically, in the embodiment, it is assumed that the body thickness correction value of the body thickness distribution Tn−1 is obtained using a steepest descent method. It is possible to minimize an output value of the error function ferror by changing only the body thickness at one specific coordinate in Tn−1(x, y) in the pixels of the virtual model K and calculating repetition dTn−1(x, y) on the basis of a first order partial derivative (gradient) of the error function ferror using Equations (11) and (12) below. The body thickness at one specific coordinate in a case where the output value of the error function ferror is minimized is determined to be the correction value of the body thickness at the specific coordinate. Further, with respect to other pixels, similarly, the body thickness distribution of each of the pixels is corrected by obtaining the correction value of the body thickness, and a corrected body thickness distribution Tn is obtained.

[Equation 8]

$$T_n(x, y) = T_{n-1}(x, y) - \alpha dT_{n-1}(x, y) \quad (11)$$
$$= T_{n-1}(x, y) - \alpha \frac{d}{dT_{n-1}(x, y)} f_{error}$$

$$\frac{d}{dT_{n-1}(x, y)} f_{error} = \quad (12)$$
$$\sum_{x',y'} (I_m(x', y') - I(x', y')) \frac{d}{dT_{n-1}(x, y)} K_{p+s}(x', y', T_{n-1}(x, y), \theta_{x,y})$$

$$\frac{d}{dT_{n-1}(x, y)} K_{p+s}(x', y', T_{n-1}(x, y), \theta_{x,y}) = \quad (13)$$
$$K_{p+s}(x', y', T_{n-1}(x, y) + dt, \theta_{x,y}) - K_{p+s}(x', y', T_{n-1}(x, y), \theta_{x,y})$$

Here, in Equation (11), α is an update coefficient which is a parameter representing an update speed of the body thickness. As an example of a method of calculating a differential value portion of Kp+s shown in Equation (12), for example, a change in value in a case where a very small value dt is added to Tn−1(x, y) can be calculated using Equation (13) and can be set as a value of Kp+s in Equation (12). In Equations (3) to (13), the same elements are denoted with the same reference signs, and description thereof will be omitted. Any optimization method of minimizing the error value Verror representing the difference between the low-frequency soft portion image GLs and the estimated image Im can be applied and, for example, a simplex method, a steepest descent method, or a conjugate gradient method can be used.

In a case where the corrected body thickness distribution Tn is acquired, the body thickness distribution determination unit 44 increments the value of n by 1 (n=n+1) to update the value, and the virtual model acquisition unit 41 acquires the corrected body thickness distribution Tn (step ST11). The estimated image generation unit 42 and the body thickness distribution determination unit 44 execute the processes of steps ST11 to ST13 for the acquired body thickness distribution Tn, similar to the above. The process of correcting the body thickness distribution Tn (step ST14), the process of acquiring the virtual model K having the corrected body thickness distribution Tn (step ST11), the process of generating a new estimated image Im using the body thickness distribution Tn(step ST12), and the process of determining whether a difference between the newly generated estimated image Im and the radiation image satisfies the end condition (step ST13) are repeated until the error value Verror indicating the difference between the low-frequency soft portion image GLs and the estimated image Im satisfies the end conditions.

On the other hand, in a case where the body thickness distribution determination unit 44 determines that the error value Verror satisfies the end condition (step ST13: Yes), the body thickness distribution determination unit 44 determines the body thickness distribution Tn used for the error value Verror in a case where the end condition is satisfied, to be the body thickness distribution T of the low-frequency soft portion image GLs, and the body thickness estimation process ends (step ST15).

Thus, in the embodiment, the soft portion image Gs is generated through the subtraction process, the low-frequency soft portion image GLs is generated from the soft portion image Gs, the body thickness distribution of the subject H is estimated on the basis of the imaging conditions in a case where the low-frequency soft portion image GLs and the radiation image are acquired, the approximate body thickness distribution obtained by approximating the estimated body thickness distribution to the elliptic cylinder model is calculated, and the distribution of the body fat percentage in the subject H is calculated on the basis of the approximate body thickness distribution. Therefore, it is possible to measure the distribution of the body fat percentage of the subject with a small number of times of imaging, and thereby, it is possible to reduce the amount of exposure to radiation of the subject H and easily measure the body fat percentage of the subject.

Further, it is possible to accurately estimate the body thickness distribution of the subject H without being influenced by a fine structure in the subject by generating the low-frequency soft portion image GLs from the soft portion image Gs and estimating the body thickness distribution of the subject H on the basis of the low-frequency soft portion image GLs and the imaging conditions.

Further, it is possible to confirm the distribution of the body fat percentage of the subject by displaying the distribution of the body fat percentage on the display unit 8. In particular, it is possible to easily confirm how the body fat percentage is distributed in a certain structure in the subject by displaying the distribution of the body fat percentage to be superimposed on the first radiation image G1 or the like. Therefore, it is possible to easily perform diagnosis using the body fat percentage.

Although the density difference distribution $\Delta(x, y)$ in Equation (2) is calculated by subtracting the density of each pixel in the area of the subject H from the density in the void area in the above embodiment, the density difference distribution $\Delta(x, y)$ may be calculated by Equation (14) below using the body thickness distribution $T(x, y)$ estimated by the body thickness estimation unit 33.

$$\Delta(x,y) = \mu_{soft} \times T(x,y) \quad (14)$$

Further, although the body thickness distribution is estimated by generating the low-frequency soft portion image GLs from the soft portion image Gs in the above embodiment, the body thickness distribution may be estimated from the soft portion image Gs without generating the low-frequency soft portion image GLs.

Further, although the first and second radiation images G1 and G2 are acquired using a one-shot method in the above embodiment, the first and second radiation images G1 and G2 may be acquired using a so-called two-shot method in which imaging is performed twice.

Further, in each embodiment, the image processing is performed using the radiation image acquired in the system for capturing the radiation image of the subject using the first and second radiation detectors 5 and 6. However, it is understood that the present invention can also be applied to a case where the first and second radiation images G1 and G2 are acquired using an accumulative phosphor sheet as a detection unit. In this case, the first and second radiation images G1 and G2 may be acquired by superimposing two accumulative phosphor sheets, irradiating the accumulative phosphor sheets with the X-rays transmitted through the subject H, accumulating and recording radiation image information of the subject H in each accumulative phosphor sheet, and photoelectrically reading the radiation image information from each accumulative phosphor sheet.

Further, in the above embodiment, the elliptic cylinder model is used as the model corresponding to the human body, but the present invention is not limited thereto. For example, a model of which the cross-section is defined by a circular, polygonal, or predetermined curve may be used as the model corresponding to the human body. Further, an average sectional shape of an axial cross-section of a human body may be calculated using an image of an axial cross-section in a computed tomography (CT) image, a magnetic resonance imaging (MRI) image, or the like, and a model having the calculated cross-sectional shape may be used as a model corresponding to the human body.

Hereinafter, an operation and effect of the embodiment will be described.

By generating the low frequency image of the soft portion image and estimating the body thickness distribution of the subject on the basis of the low frequency image of the soft portion image and the imaging conditions, it is possible to accurately estimate the body thickness distribution of the subject without being influenced by a fine structure in the subject.

It is possible to confirm the distribution of the body fat percentage of the subject by displaying the distribution of the body fat percentage. In particular, it is possible to easily confirm how the body fat percentage is distributed in which structure in the subject by displaying the distribution of the body fat percentage to be superimposed on any of a plurality of radiation images. Therefore, it is possible to easily perform diagnosis using the body fat percentage.

EXPLANATION OF REFERENCES 1 imaging device for radiation image
2 computer
3 X-ray source
5, 6 radiation detector
7 X-ray energy conversion filter
8 display unit
9 input unit
21 CPU
22 memory
23 storage
31 image acquisition unit
32 subtraction processing unit
33 body thickness estimation unit
34 approximate body thickness distribution calculation unit
35 body fat percentage calculation unit
36 display control unit
41 virtual model acquisition unit
42 estimated image generation unit
43 correction unit
44 body thickness distribution determination unit
50 arrow
51 soft portion tissue
52 fat
55 reference
G1 first radiation image
G2 second radiation image
Gs soft portion image
GLs low-frequency soft portion image
H subject

What is claimed is:

1. A body fat percentage measurement device comprising:
a processor configured to:
generate a soft portion image representing a soft portion tissue of a subject from a plurality of radiation images acquired using X-rays having different energy distributions transmitted through the subject;
estimate a body thickness distribution of the subject on the basis of imaging conditions in a case where the soft portion image and the radiation images are acquired;
generate a filtered image of the soft portion image using a filter;
estimate the body thickness distribution of the subject on the basis of the filtered image of the soft portion image and the imaging conditions;
calculate an approximate body thickness distribution obtained by approximating the estimated body thickness distribution to a model having a cross-section corresponding to a cross-section of a human body;
generate the model having the cross-section corresponding to the cross-section of the human body using the calculation of the approximate body thickness distribution; and calculate a distribution of a body fat percentage in the subject using the approximate body thickness distribution and an attenuation coefficient of the soft portion tissue of the subject.

2. The body fat percentage measurement device according to claim 1,
wherein the processor further calculates the distribution of the body fat percentage on the basis of the estimated body thickness distribution.

3. The body thickness estimation device according to claim 1,
wherein the processor is further configured to display the distribution of the body fat percentage on a display.

4. The body thickness estimation device according to claim 2,
wherein the processor is further configured to display the distribution of the body fat percentage on a display.

5. The body fat percentage measurement device according to claim 3,
wherein the processor displays the distribution of the body fat percentage to be superimposed on any one of the plurality of radiation images and the soft portion image.

6. The body fat percentage measurement device according to claim 4,
wherein the processor displays the distribution of the body fat percentage to be superimposed on any one of the plurality of radiation images and the soft portion image.

* * * * *